United States Patent [19]

Sweeney

[11] Patent Number: 4,833,171

[45] Date of Patent: May 23, 1989

[54] SYNTHESIS GAS SYSTEM

[76] Inventor: Maxwell P. Sweeney, 1817 Fanning St., Los Angeles, Calif. 90026

[21] Appl. No.: 690,434

[22] Filed: Jan. 10, 1985

Related U.S. Application Data

[63] Continuation of Ser. No. 228,908, Jan. 27, 1981, abandoned.

[51] Int. Cl.$^4$ .............................................. C07C 1/02
[52] U.S. Cl. .................................. 518/703; 518/704; 252/373
[58] Field of Search ................ 252/373; 518/703, 704

[56] References Cited

U.S. PATENT DOCUMENTS

| | | | |
|---|---|---|---|
| 4,099,383 | 7/1978 | Paull et al. | 252/373 |
| 4,203,915 | 5/1980 | Supp et al. | 252/373 |
| 4,271,086 | 6/1981 | Supp et al. | 252/373 |

Primary Examiner—Alan Siegel
Attorney, Agent, or Firm—Albert L. Gabriel

[57] ABSTRACT

Method and apparatus for the production of synthesis gas from hydrocarbonaceous gases, wherein a hydrocarbonaceous gas is preheated, reacted with oxygen in the presence of steam, and quenched utilizing a rotating matrix comprising glassy ceramic fibers. After reaction with oxygen, the gases may be passed over a catalyst to further convert said hydrocarbonaceous gas to synthesis gas. Such method and apparatus is especially useful in a process for the production of methanol, wherein carbon dioxide in the synthesis gases is absorbed using crude methanol and recycled, by stripping the $CO_2$-rich crude methanol with gas which has passed over catalyst for the conversion of synthesis gas to methanol under conversion conditions, thereby recycling and ultimately recovering as methanol yield carbon present in both carbon dioxide and unconverted methane present in said gases. This process requires neither the expensive reforming furnace nor the expensive synthesis gas compressors conventionally required in steam reforming methods, and uses much less oxygen than in conventional partial oxidation processes. This process is usefully augmented by additional methanol production by means of method and apparatus for partial oxidation, thereby comprising an even more highly efficient, integrated process for the production of methanol, wherein all methane carbon utilized by the combined process is converted to methanol except for about 7% which is required as fuel for power in efficiently separating the oxygen required from air and compressing it to operating pressure.

3 Claims, 2 Drawing Sheets

SYNTHESIS GAS SYSTEM

RELATED APPLICATION

This is a continuation of application Ser. No. 228,908, filed Jan. 27, 1981 now abandoned.

This application is being filed concurrently with my application entitled PARTIAL OXIDATION SYSTEM, Ser. No. 228,909, a copy of which is appended hereto and which is hereby incorporated by reference in its entirety in the present application.

BACKGROUND OF THE INVENTION

1. Field of the Invention

The invention is in the field of synthesis gas and methanol production.

2. Description of the Prior Art

Hydrocarbonaceous materials, including pertroleum oil and natural gas, coal and the like—i.e., fossil energy—are becoming much more expensive and of lower availability. As long as petroleum oil was plentifully available transportation and other liquid fuels could readily be obtained by well-known and relatively inexpensive refining processes.

But with increasing scarcity such refined liquid fuels will no longer be sufficient. Much research and development effort has been expended to supplement such fuels. It is, for example, well known that "synthesis gas"—a mixture of mainly carbon monoxide and hydrogen—may be converted particularly over appropriate catalyst, to a wide variety of increasingly valuable products, including hydrogen, carbon monoxide, ammonia, and hydrocarbonaceous and oxyhydrocarbonaceous liquids. Possible liquid products include methanol, ethanol, higher alcohols, ethylene glycol, and liquid hydrocarbons. For the most part they can either be used directly or further converted to chemical products or to liquid fuels.

This synthesis gas may be—and has been—derived from any of the hydrocarbonaceous raw materials by reacting these with steam and/or oxygen at relatively high temperatures. However, the great disadvantage of such prior processes, particularly those which convert one fuel into another fuel, is that the thermal energy efficiency is relatively low: one ends up with substantially less fuel heating value than one started with. The state-of-the-art processes are thus wasteful of increasingly scarce and expensive fossil energy.

Thus, in a recent, carefully engineered, state-of-the-art comparison by the broadly experienced Lurgi Company ["Gasoline Production from Natural Gas or Coal," E. Supp, 1980, Table II], the following thermal efficiencies (based on the lower heating values of starting materials and end products—with by-product electricity calculated back to equivalent heat on a reasonable basis) are shown to be economically attainable.

| | Thermal Efficiencies, % | | | |
|---|---|---|---|---|
| | Case: | | | |
| | I | II | III | IV |
| | Raw Material: | | | |
| Products | Natural Gas | | Coal | |
| Methanol | 61.8 | 66.5 | 48.6 | |
| Methanol + Electricity | 62.9 | | | |
| Methanol + Methane Fuel | | | | 58.4 |

| | Thermal Efficiencies, % | | | |
|---|---|---|---|---|
| | Case: | | | |
| | I | II | III | IV |
| | Raw Material: | | | |
| Products | Natural Gas | | Coal | |
| Gasoline | 56.1 | 64.5 | 46.2 | |
| Gasoline + Electricity | 57.6 | | | |
| Gasoline + Methane Fuel | | | | 55.8 |

In Case I, conventional steam reforming of natural gas to produce synthesis gas, which is then compressed and catalytically converted to methanol, is utilized. For the production of gasoline, the methanol is catalytically converted using the Mobil Corporation methanol-to-gasoline (MTG) process.

Case II is similar except that oxygen is added in a second stage of (autothermal) reforming. Case III autothermally reforms coal with steam and oxygen; and, in Case IV, the purge gas is catalytically methanated to form a synthetic natural gas. In all cases fuel necessary for all utilities required in the process is furnished and included in the calculations.

Several significant conclusions are apparent from the values given above. First, the above approaches to the conversion of coal to more useful liquid fuels has a higher thermal efficiency than other methods: Fischer-Tropsch (about 40%) and (improved) coal hydrogenation (about 54%). Second, natural gas is much more efficient as a raw material than coal. In terms of energy losses—in comparing the highest values given, using coal loses over 24% more energy than in using natural gas. Conservation of overall energy considerations therefore favor using natural gas for this purpose—provided of course that there are other uses for coal in which its relative thermal efficiency is higher than in the above use. (Such a use is indeed direct generation of electricity in steam-electric stations, where coal should displace natural gas. For their thermal efficiencies are about equal).

In addition, the overall capital investment cost for the use of coal to produce liquid fuels is about three times that for use of natural gas. In consequence of both of these factors—in which coal wastes both scarce energy and scarce capital—natural gas cost would have to rise to about six times the cost of coal before coal becomes economically competitive for these purposes. Fortunately, it has been estimated that sufficient natural gas has been, or is still to be, found in the world so that it is nearly as plentiful as coal is, so that, from an economic standpoint for many decades hence, natural gas will be favored for these purposes.

Next, it is seen that an excess of relatively low temperature by-product heat is produced, which can be converted into electricity, in Case I, that of conventional steam reforming. However, such does not improve the overall thermal efficiency greatly. A much better practice is to go to Case II. This, however, would require the added investment of an air-separation oxygen plant and compressor, which has seldom been economically justified or practiced.

Finally, it is seen that even with the various combinations thermal efficiencies are still quite low and represent a very substantial loss of energy.

SUMMARY OF THE INVENTION

In view of the above, it is a general object of the present invention to provide a novel method and apparatus for more efficiently producing synthesis gas from natural and other similar gases, wherein the thermal efficiency is substantially raised.

In the production of methanol from methane gas by the preferred integrated process as hereinafter described, for example, it will be shown that losses of carbon feed-and-fuel conversion efficiency can be lowered by about a factor of four from that of the conventional steam reforming; i.e., from a loss of about 28% of carbon in feed-and-fuel to as low as about 7% (corresponding then to an overall thermal efficiency as high as about 80%, on a comparable basis to those given above).

Another object of the invention is to utilize most efficiently the inherent pressure of most natural gas as it is produced from its source.

Another object of the invention is to reform the feed under pressure sufficiently high so that the synthesis gas needs no compression for many of its uses, for example usually including production of hydrogen, carbon monoxide, methanol, and gasoline by MTG.

Thus it will be understood by those skilled in the prior art that in conventional steam reforming—which is highly endothermic, and in which the feed gas is heated inside catalyst-filled tubes in a large fired furnace—the allowable tubewall temperatures are strictly limited, in spite of the use of very expensive materials therefor. And further it is well known that the steam reforming reaction:

$$CH_4 + H_2O \rightarrow CO + 3H_2,$$

by virtue of its production of four molecules from two, is highly adversely affected by pressure; i.e., the reaction tends to reverse in proportion to the square of the pressure.

In consequence conventional steam reforming methods have been limited to the range of about 18-30 atmospheres of pressure, and thus require compression of this large volume, low molecular weight gas in many stages of centrifugal compressors.

Another object of the invention is, in the desired production of methanol only, to eliminate the excess production of hydrogen. Thus in catalytic methanol production by the reaction:

$$CO + 2H_2 \rightarrow CH_3OH,$$

a ratio of $H_2/CO$ of 2 is desired, whereas by the above steam-reforming reaction, a ratio of 3 is produced. This excess hydrogen requires excess venting of gases purged from the methanol converter and carries with it undue losses of methanol vapor and other carbon as well as hydrogen. In addition, this excess hydrogen produces a highly non-optimum converter gas composition, much higher than the 3 to 1 of the makeup gas—by virtue of the removal of 2 to 1 in the form of methanol.

It is another object of the invention to produce and consume heat at maximum economic efficiency such that no excess low level heat is wasted.

It is another object of the invention to utilize autothermal production of synthesis gas wherein the total oxygen required is conserved to only a fraction of that required by usual autothermal synthesis gas processes.

Another object of the invention is to optimize the composition of the makeup synthesis gas to a methanol converter such that the methanol formation rate over the catalyst is maximized, and such that all of the gas required to be purged therefrom is usefully utilized in providing motive power for the process, including compression of air for the air separation plant and compression of the oxygen therefrom.

Another object of the invention is to provide a "backup" safety means for further lowering the content of deleterious methanol catalyst poisons, particularly sulfur compounds including $H_2S$ and COS, thereby increasing catalyst life (especially that of the extremely sensitive modern, so-called 'low temperature' catalysts for methanol production).

Another object of the invention is to provide a methanol converter that will permit catalytic conversion at much larger capacities in a single vessel than heretofore practical in exothermic reactions, in which at least a substantial portion of the heat released by and during the course of the reaction is absorbed by tubular flow of liquid being thereby heated or boiled.

Another object of the invention is to provide an integrated process and apparatus means for the production of methanol from natural gas which is capable of very high capacities, and yet is relatively very compact, being thereby suitable for the substantial and efficient production of liquid fuel from natural gas at remote sites, including barge-mounted and other offshore units.

According to the invention, synthesis gas is much more efficiently produced by preheating the hydrocarbonaceous gas feed to a temperature in excess of 1500° F., autothermally reacting the hydrocarbonaceous gas with oxygen in the presence of steam and then reforming the hydrocarbonaceous gas. Thus, in direct contrast to the conventional steam reforming method, no intentional reforming is undertaken below 1500° F., or during heat exchange heating. In consequence, the requirements for both steam—as compared to conventional steam reforming—and oxygen—as compared to so-called partial oxidation systems—are minimized and it becomes practical to conduct the reforming reaction under such high pressures that subsequent necessary compression of the synthesis gas is minimized, and in many practical uses of the synthesis gas, eliminated entirely. This is an important economic advantage because these compressors are large and very expensive, and of course, require substantial energy.

Preferably, according to the invention, the preheating step in the reforming of the hydrocarbonaceous gas is accomplished by heat exchange with the reformed product of the reforming reaction. And preferably this heat exchange is accomplished by utilizing a radial flow rotary heat renerator, the matrix of which is comprised of ceramic fibers in glassy form, the construction of which is described in my said co-pending application Ser. No. 228,909. In this way the contact material in the heat exchange step is inert to the carbon deposition, Boudouard reaction, as more fully explained hereinafter in the Detailed Description. Furthermore it is preferred that oxygen also be preheated in a portion of the rotating matrix so that not only is heat conserved, but also so that any carbon which is deposited on the matrix will be gasified by oxygen, so as to ensure that no plugging by carbon can occur.

Next, according to an important aspect of the invention, the steam which is required in the reforming step is generated by passing the hydrocarbonaceous gas feed, along with liquid water, in heat exchange relationship with a heat-producing catalytic reaction of the synthesis gas or a gas derived from the synthesis gas. This important step produces the steam in the reformer reactant gas at a higher total pressure than would be possible by generating steam separately and adding it to the reactant gas, and again aids in eliminating synthesis gas compressors, especially in the production of methanol from the synthesis gas.

According to another important aspect of the invention, the step of producing heat in such a heat-producing catalytic reaction, and recovering it usefully, while thereby controlling the temperature therein, is advantageously accomplished in a novel radial flow catalyst bed structure with transverse heat-absorbing tubes, thereby not only controlling the average bed temperature but also the temperature profile along the radial flow path. This structure also lends itself to highly practical means of dumping old catalyst, and replacing it with new.

Another aspect of the invention concerns the carbon dioxide product of the reforming reaction. Thus, the water gas shift equilibrium prevailing under reforming conditions requires that $CO_2$ be present in accordance with equilibrium of the reaction: $CO + H_2O = CO_2 + H_2$. For a given ratio of $H_2/CO$ (about 2), $CO_2$ required is proportional to steam. Thus minimizing steam requirement as the present invention does also minimizes $CO_2$; however, that which remains still requires excessive hydrogen to produce methanol according to the reaction: $CO_2 + 3H_2 = CH_3OH + H_2O$, and produces unwanted water in the methanol.

According to a preferred aspect of the invention in producing methanol from synthesis gas, therefore, carbon dioxide in the synthesis gas is absorbed using a liquid absorbent, and the carbon dioxide is then stripped therefrom and returned to the reforming zone, so that the net production of $CO_2$—and water in methanol—becomes minor or negligible. It is advantageous to use the crude methanol itself as the liquid absorbent.

Furthermore, since the synthesis gas comprises unreformed methane as well as carbon monoxide and hydrogen, and since this methane is inert to and builds up in the methanol conversion recycle loop, it is another aspect of the invention to use hot catalytic converter offgas—especially with its methanol vapor content—as a stripping agent to strip the $CO_2$ from the $CO_2$-rich absorbent. Not only does this step supply stripping gas and heat, but it also recycles unreformed methane to the reforming zone.

To further reduce the unreformed methane buildup as an inert in the methanol converter recycle loop, and yet to preserve the hydrogen content of this gas so that its ratio to carbon monoxide can be optimized—at greater than 2, while its production ratio is only about 2, according to the invention crude methanol is flashed to a lower pressure than the methanol synthesis pressure, thereby selectively flashing off the higher content of dissolved methane, and then a least a portion of this crude methanol is recycled and further contacted with the converter gas.

According to the invention in the preferred embodiment for the production of methanol, the net production of crude methanol being negligible in sulfur content, is advantageously used to contact the synthesis gas, thereby removing sulfur-containing contaminants therefrom, and thereby protecting the extremely sulfur-sensitive modern so-called "low temperature" catalysts for the conversion of synthesis gas to methanol. Furthermore, by taking the final net make of crude methanol directly from the hot $CO_2$-lean methanol after it has been heated and stripped of $CO_2$, and then stripping it with the (essentially sulfur-free) methanol converter offgases which are being purged from the system in order to remove inerts, including nitrogen, argon, and unreformed methane, sulfur-containing, as well as other contaminants are stripped from the product methanol, thereby obviating its contamination, without the expenditure of appreciable additional energy.

In another important aspect of the preferred embodiment of the invention, the aforesaid reforming/catalytic conversion method is combined with the direct production of methanol from methane by partial oxidation according to my said co-pending application, Ser. No. 228,909. This combined process has numerous advantages as more fully explained below in the Detailed Description, and the partial oxidation method cooperates in several beneficial ways with reforming/catalytic method. Thus, it furnishes heat thereto as well as methanol, and thereby aids in stripping $CO_2$ from the $CO_2$-rich absorbent, and in purifying the methanol, as well as producing an already partially reformed offgas therefrom.

As shown below, all the means of this invention cooperate to produce and consume synthesis gas at extremely high efficiency, as particularly shown in the case of methanol production—in which an overall yield of over 93% is attained, as compared to a state-of-the-art yield of about 72%. Similar advantageous conservation of energy will occur in other uses of synthesis gas, such as the production of hydrogen, ammonia, etc.

Further objects and advantages of the present invention will appear during the course of the following part of the specification, wherein the details of the method and apparatus of presently preferred embodiments are described with reference to the accompanying drawings, in which:

DETAILED DESCRIPTION

Methanol Process

Figure 1:
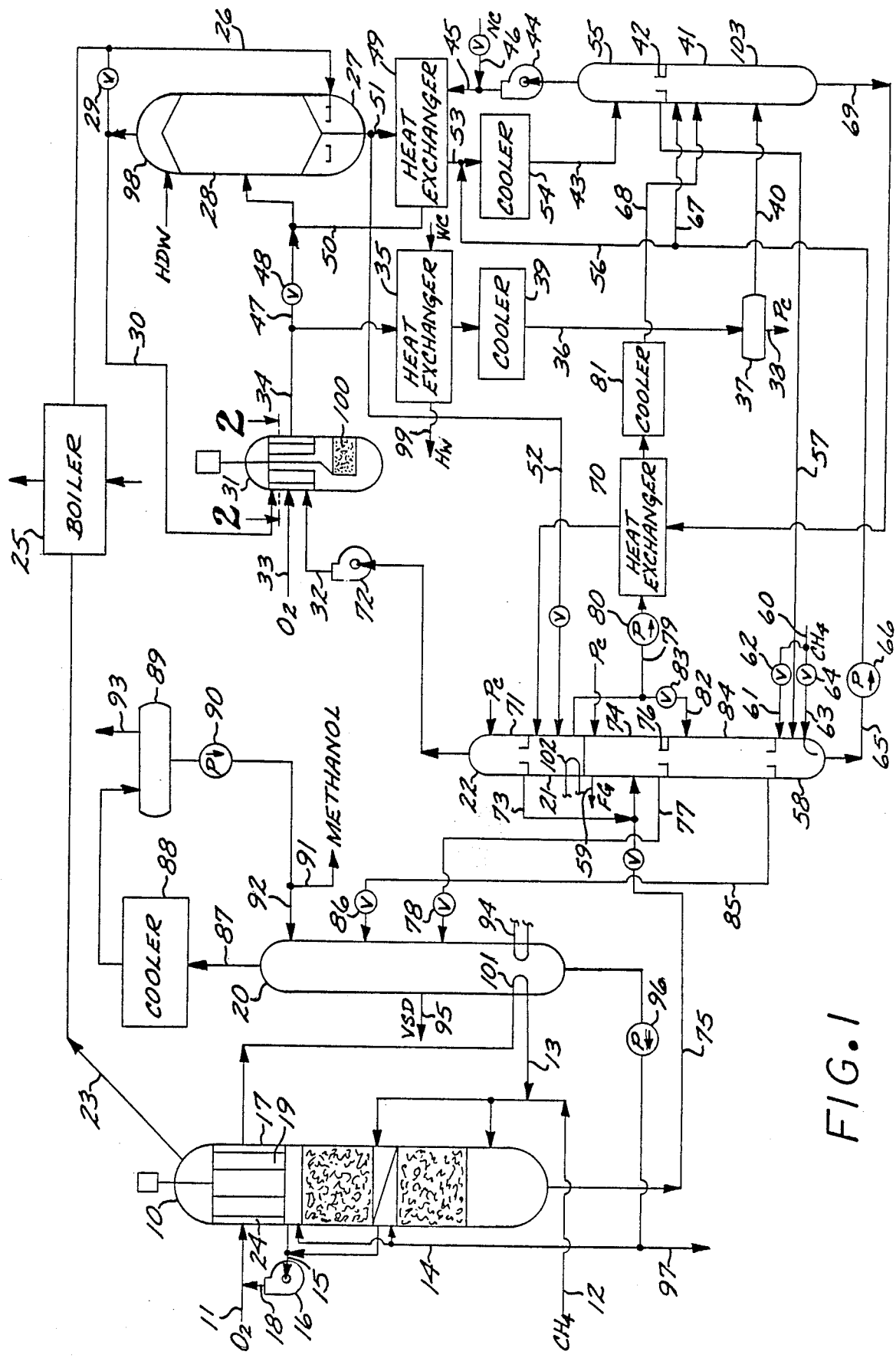
FIG. 1 is a flow diagram of the preferred embodiment of the present process for the production of synthesis gas and methanol in accordance with the present invention in combination with method and apparatus described and specified in my said concurrently filed, co-pending application Ser. No. 228,909 appended to this application and incorporated herein by reference.

Referring to FIG. 1, gas feed in line 12, preferably high methane natural gas, under a pressure preferably in the range of from about 30 to about 150 atmospheres absolute (ata), and more preferably in the range of from about 50 to about 80 ata, is introduced to recycling reaction offgas in line 13, thereby further cooling it, and the mixture is scrubbed by scrubbing water entering vessel 10 from line 14 to remove primarily methanol produced by partial oxidation of methane as described in detail in my said co-pending application Ser. No. 228,909, appended hereto and incorporated herein by reference. Schematically shown in vessel 10 are two sections of parallel countercurrent scrubbing such as would be practical for large capacity units (for example, over 1500 tons per day of total methanol capacity). These sections may be bubble plate or packed sections, as is well known in the art.

The scrubber offgases 15 from vessel 10 are circulated by recycle blower 16, and the main portion is preferably mixed with compressed oxygen in line 11 such that the mixture comprises between about 0.5 mol percent and 5 mol percent oxygen, preferably 1-3 percent (produced by an air separation plant—including an air compressor and oxygen compressor, which are preferably powered by steam and/or gas turbines, which in turn obtain their steam and fuel at least mainly from the process—all not shown), just prior to entering exchanger-reactor 17, shown schematically in FIG. 1. As described in said co-pending application appended hereto, exchanger-reactor 17 is preferably a radial flow rotary regenerative heat exchanger, rotating at between 2 and 20 RPM, preferably 5-12 RPM, with a reaction space towards the center thereof.

In the matrix 19 of reactor 17 the gas mixture is heated from about 250° F. to an average temperature of preferably between about 900° F. and about 1200° F. Because this matrix comprises a greatly extended surface, preferably multiple layers of (inert) ceramic or glass cloth, reaction by partial oxidation therein is inhibited and is minimal. As the reactant gas issues from the matrix 19, however, it is at a sufficient temperature so that it will rapidly self-accelerate in reaction rate and relatively quickly (0.1 to 2 seconds) consume substantially all of the oxygen. This exothermically reacted mixture has gained substantially in temperature, approximately in proportion to its original oxygen content, and this is now hotter than the matrix 19 which preheated it. It passes back through matrix 19, giving up sensible heat, down to a temperature of between about 325° F. and about 500° F., preferably between about 380° F. and about 450° F.

It then gives up heat usefully, as for example in reboiling duty, as schematically shown in FIG. 1, in which it supplies heat in a heat exchange loop 101 to the fractionator-stripper 20, and in a heat exchange loop 102 to the $CO_2$ stripping section 21 of the stripper-absorber 22. Such series with respect to flow in line 13 may be either in series or parallel, but will usually most advantageously be in series with flow in line 13 first furnishing higher temperature heat to the bottom of section 21. As flow in line 13 is finally cooled in such useful duty, substantial water and some methanol products of the partial oxidation reaction are condensed, thereby augmenting by their latent heat the sensible heat recovered. As will further be seen below virtually all of the heat release of the partial oxidation reaction is thus usefully recovered. Furthermore it will be seen that each increment of heat is recovered at virtually as high a temperature as possible, thus contributing significantly to the high overall thermal efficiency of the process.

Under these partial oxidation reaction conditions of high ratio of methane to oxygen and relatively high pressure, the main overall reaction is:

$$CH_4 + \tfrac{1}{2}O_2 = CH_3OH + 30.1 \text{ Kcal/gm-mol.}$$

As described in said co-pending application appended hereto, under preferred conditions methanol is produced at high conversion selectivity from methane, along with minor amounts of formaldehyde, carbon monoxide and water vapor and very small amounts of carbon dioxide, hydrogen, formic acid, hydrogen peroxide, dimethyl-ether, dimethyl peroxide, and the like. The presence of such minor constituents in the recycle gas in line 18 will substantially assist initiation of the free radical reactions involved in the partial oxidation, since they are all (except for carbon dioxide and water) more reactive in this environment than is methane itself.

In the scrubbing operation referred to above, of the above minor constituents, only formic acid, hydrogen peroxide and formaldehyde will appreciably dissolve in scrubbing water in line 14, and, being less volatile than methanol in the presence of water, will remain in the scrubbing water and will ultimately contribute to the formation of synthesis gas, as described in greater detail below. Minor products not scrubbed out will be mostly recycled, with the net offgas flow in line 18 from vessel 10 with its content of minor constituents, also providing their contribution to synthesis gas formation.

Thus methanol of substantial purity only is produced as ultimate product from this partial oxidation unit. Although methanol can very advantageously be produced in the rest of the process without using this partial oxidation unit—and such is contemplated by the present invention—its inclusion in combination with the rest of the process has numerous advantages.

First, by its heat release, it acts somewhat in the manner of a furnace, but superior thereto. Thus it generates heat directly in the stream being processed rather than in another (combustion) stream which is ultimately discarded, thereby losing potential heat and product. Second, even latent heat of condensation is quite readily recovered—as referred to above, which can virtually never be readily or practically accomplished in the combustion products from a furnace. Third, and most important, it is a "furnace" in which methanol is produced as a recovered product, rather than carbon dioxide which can very seldom be economically recovered or usefully utilized from combustion gases.

Fourth, it supplies a balance in the overall methane/oxygen ratio to the entire process such that the overall reaction in the entire process is essentially: $CH_4 + \tfrac{1}{2}O_2 = CH_3OH$; thus providing the most efficient possible utilization of both feed carbon and hydrogen atoms. The reason why it supplies such balance is that the actual partial oxidation reaction itself consumes more oxygen than the indicated one-half mol per mol of methane reacted, while the subsequent production of synthesis gas, as taught by this invention, requires less.

Fifth, to the extent that the minor products which are produced in the partial oxidation reaction are carbon monoxide and/or hydrogen a direct reforming has already been accomplished, thereby relieving load from subsequent reforming requirements. In addition, any formaldehyde and the like which is formed and which ultimately passes to reforming either in aqueous solution or in the gaseous feed thereto will therein very readily reform without the appreciable need for oxygen, steam or heat supply to an endothermic reaction, for the reaction: $CH_2O = CO + H_2$ is virtually thermoneutral.

Finally, this internally-generated-heat "furnace" preheats the offgas 23 therefrom which is feed to the reforming section. Indeed, the preheat which can readily be supplied will usually be more than sufficient for the next processing step, permitting some heat content therein to be recovered therefrom in the form of high pressure steam (preferably 900 psia or higher), thereby not only supplying such where required to the process itself, but also providing for the production of motive power required therein.

Offgas in line 23 is preferably obtained from the output (in line 18) of recycle blower 16 without admixture with oxygen. As detailed in said co-pending application appended hereto, this gas passes via a line (not shown) to one or more separate sections of the plenum chamber 24, preferably passes inward through an isolated section of matrix 19, into a separate collecting inner plenum (not shown) which communicates with the outlet from the vessel shown as line 23. The matrix 19 can, and preferably does, preheat this offgas to a temperature higher than the average preheat given by matrix 19 to the total gas being heated thereby, by locating the aforesaid separate section or sections of the plenum chamber 24 at one or more respective points in respect to the direction of rotation of the matrix such that the matrix has just been heated by relatively hot, outflowing gas immediately before being contacted by this offgas to be preheated.

Preferably, then, offgas in line 23 passes through boiler 25, giving up heat thereto, and then at least the major portion thereof passes by line 26 to the waterside 27 of methanol converter vessel 28. The construction and operation of this converter 28 is described in detail below, by reference to FIG. 4.

The gas from line 26 in admixture with hot process water causes some of this water to vaporize into this gas and the mixture passes up through tubes, disengages from the water after said passage and the gases, now saturated with water (and any other constituents in the water), joins any flow desired through valve 29, and this gaseous mixture in line 30 becomes the main feed to a reforming vessel 31. By regulating the flow through valve 29, any desired water vapor content of the gases in line 30 may be obtained up to saturation of the total gas therein at the temperature of the water at the point of disengagement.

If additional water content were required in the total gas which is fed to reforming vessel 31, recycle gas in line 32 could also be introduced to waterside 27 of vessel 28, and thus also pick up its complement of water vapor. However, such a modification, while quite feasible and within the present scope, will usually not be necessary in this preferred embodiment for the production of synthesis gas and methanol. The reasons why a relatively very low ratio of water to carbon is permissible in this embodiment as compared to conventional steam reforming is further explained in detail below. It suffices to remark at this point that this low process steam requirement is a substantial contributing factor to the very high feed-and-fuel yield efficiency (over about 93%) of this preferred embodiment for the production of synthesis gas and methanol. Thus, in conventional steam reforming, where steam must be produced and mixed with process gases beyond the amount or pressure of steam that can be generated from the heat release of the methanol production reaction, in general requires compression of the relatively high volume of synthesis gas and excessive wasteful condensation of water from the reformed gases at lower temperatures than those of its generation, by virtue of the increased volume and the admixing itself.

In vessel 31, gas from line 30 comprising mainly methane and steam, recycle gas from line 32, comprising mainly carbon dioxide, and oxygen from line 33 are preferably each separately preheated, then are combined together, during which a series of reactions take place which are at first highly exothermic, as the oxygen in effect "burns" in an excess of hydrocarbons—as well as steam and $CO_2$, and then the steam and $CO_2$, at first rapidly and then more slowly endothermically combine with remaining hydrocarbons; for example, according to the following reactions:

$CH_4 + H_2O = CO + 3H_2 - 49.3$ Kcal/gm-mol $CH_4 + CO_2 = 2CO + 2H_2 - 59.2$ Kcal/gm-mol.

The detailed construction and operation of the vessel 31 are described below by reference to FIGS. 2 and 3. Actually, as will be seen below, on an overall basis within vessel 31 very little if any of the second, highly endothermic, of the above reaction occurs. (Indeed, depending upon $CO_2$ production in the partial oxidation section in reactor 17, this reaction may even slightly reverse). Thus, as will be further seen below, the great bulk at least of the $CO_2$ required in the complex equilibriums involved, such as, for example, that of the water gas shift reaction: $CO + H_2O = CO_2 + H_2$, is preferably furnished to the reform reaction environment not by production therein, but by recycle. Again this recycle operation is a contributing factor to the high yield, since in the production of synthesis gas, $CO_2$ is to be regarded more as a contaminant rather than as a desired constituent. For example, in the production of methanol from synthesis gas, production of methanol by the reaction: $CO_2 + 3H_2 = CH_3OH + H_2O$ is wasteful of hydrogen and produces unwanted water in the methanol product. In addition, high $CO_2$ contents in the gas over the methanol conversion catalyst tends to inhibit the desired reaction: $CO + 2H_2 = CH_3OH$. Even further, a substantial loss of $CO_2$ from the overall process, as for example in purge gas from the methanol converter signifies a loss of both carbon and oxygen from the process.

After the above reforming reactions occur homogeneously in vessel 31 to a substantial extent, the temperature by virtue of the endothermicity of these reactions, has dropped to the point (below about 2300° F.) where the rates of these homogeneous reactions become relatively slow, and then the reforming reactions are completed over a so-called secondary reforming catalyst, which catalysts are well known in the art and readily available commercially (for operation, it is said, up to a maximum temperature of 1300° C.; i.e., 2372° F.). The offgases leave this secondary catalyst preferably at a temperature of 1900° F.–2100° F., pass back in heat exchange relationship to incoming gases, giving up sensible heat thereto, and exit at a temperature of preferably 550° F.–900° F., more preferably 570° F.–650° F. At these relatively quite low temperatures the synthesis gases have little or no appreciable tendency (even over metals) to reestablish equilibriums corresponding to this temperature—which equilibriums would tend to deposit carbon by the Boudouard reaction: $2CO = CO_2 + C$, or re-form methane by the reverse of the reforming reactions given above.

It is to be emphasized that this method of producing synthesis gas is not only highly efficient but uniquely solves the difficult problems in connection therewith. First, as mentioned above, when hot synthesis gas is cooled, the carbon monoxide therein strongly tends to deposit carbon according to the Boudouard reaction: $2CO=CO_2+C$. This carbon formation plagues the exisitng (autothermal) processes which cause oxygen to form synthesis gas at a relatively high temperature. The process of the present invention avoids these problems in three ways:

(1) Below about 1700° F. when, in the preferred embodiment, equilibrium according to the Boudouard reaction will tend, more and more strongly as the temperature is lowered, to form carbon, the synthesis is in the midst of the glassy ceramic fiber heat exchange matrix, where it is being very rapidly cooled. Now the Boudouard reaction is strongly catalyzed by metal surfaces, especially those of Group VIII, the transition metals, particularly including the common high temperature construction metals iron and nickel. Thus, one cannot recover heat from the hot synthesis gas utilizing heat transfer through metal surfaces. On the other hand, non-reducible and non-oxidizable ceramic oxides are virtually non-catalytic to this reaction; but, of course they are poor heat conductors and hence could not be particularly effective for transfer of heat by recuperative means, but only by the regenerative means of the present invention.

(2) The conventional steam reforming process requires external heating through metal tube walls and only avoids carbon deposition during synthesis gas formation by the use of relatively very large amounts of steam, and it can recover heat from the hot synthesis gas only by maintaining heat recovery metal tube walls below about 650° F. (by boiling water), where the Boudouard reaction is now limited by a very low reaction rate even in the presence of metals. The subject process, in contrast, does not form carbon monoxide during the heating phase—consequently avoiding the high steam requirement—is able to recover heat at much higher temperatures, and delivers the synthesis gas itself—for further cooling in the presence of metal walls—below a temperature of 900° F., where the reaction is reasonably slow, and preferably below about 650° F., where the Boudouard reaction is no longer any significant problem.

(3) Within the range of cooling of about 1700° F. to about 900° F., or preferably about 1700° F. to about 650° F., is then the critical temperature range for carbon deposition, and it must be emphasized that only a very minor rate of deposition such as might be expected from a "non-catalytic" surface would, in a relatively short time—possibly of the order of minutes, plug up a regenerative heat exchanger. In overcoming this problem with certainty, several of the elements of the preferred embodiment cooperate. First the matrix of the preferred regenerator is not only comprised of "inert" materials, but it is also fibrous, and hence will filter out such carbon as is formed near its point of formation—thereby obviating any downstream problems. Next, preferably rotating at about 5 RPM or more and being preferably regenerated in each revolution, an amount of deposition corresponding only to less than about 12 seconds of matrix contact time with synthesis gas will occur. Finally, in the preferred embodiment, not only are the hydrocarbonaceous feed gases and steam (and $CO_2$) preheated, but also the oxygen by the same subject matrix. Thus, any deposited carbon will be quickly and completely burned off by this essentially pure, compressed oxygen. No plugging problem can then occur, and all problems connected with the instability of synthesis gas, and the efficient recovery of heat therefrom, are solved without the use of excessive amount of steam—only that amount being required which is required by equilibrium considerations at the temperature of formation, which will always be above about 1500° F. and preferably above about 1900° F., where synthesis gas is at its highest stability.

Next, offgases in line 34 are preferably cooled by heat exchange in various stages with water boiling at one or more pressures convenient to the process and are also cooled by preheating such water streams as are convenient to the process. All these stages are symbolized by heat exchanger 35, and by heat exchange loop 94, which is boiling essentially water at the bottom of fractionator-stripper 20, using heat from these offgases. During much of the latter part of this cooling, water condenses from the gases, and is separated out at one or more convenient points. This separation is symbolized by the offgases in line 36 passing through separator 37, where condensate is removed via line 38. After final cooling with cooling water or other medium in exchanger 39, preferably to below about 110° F., the now-relatively-dry gases in line 40 enter separator-absorber vessel 41. In the bottom section of this vessel 41, the gases are counter-currently contacted with an absorbent for $CO_2$ in an amount, and with sufficient stages in the absorber, such that most of $CO_2$ is preferably absorbed into said absorbent. In the case of this preferred embodiment for the production of methanol, it is preferred that the absorbent is crude methanol itself, thus, in addition to other advantages, obviating any possible contamination of product methanol with absorbent. This crude methanol, as produced by the methanol converter, is also essentially completely sulfur free and will tend also to absorb any sulfur compounds, including $H_2S$ and COS, both of which are more soluble in methanol than $CO_2$, thereby tending to minimize the deactivation of these highly sulfur sensitive modern so-called 'low temperature' methanol conversion catalysts.

After absorption, the synthesis make gas in this preferred embodiment passes up through riser 42 and joins converter recycle gases from line 43. These gases then pass through circulating blower 44. Phineas Davies, et al (U.S. Pat. No. 3,326,956, issued June 20, 1967) teaches that a certain small amount of $CO_2$ is desirable in gases over methanol converter catalysts. Partly because water and $CO_2$ are are interconvertible by the water gas shift reaction given above—and the 'low temperature' methanol converter catalysts are active as a catalyst for this reaction, a small, controlled amount of (relatively pure) water condensate is shown in FIG. 1 being sprayed into line 45 via line 46. It will be found that such a procedure is at least as efficacious as the use of $CO_2$ in preventing deleterious reduction in catalyst activity by the non-introduction of appreciable $CO_2$. If desired, of course, it is also within the scope of this invention either to lower the effectiveness of the absorption step or to utilize a small controlled bypass (not shown) of offgases around the absorber. Indeed, such a bypass before cooling the offgases, passing directly to the inlet of the methanol converter via line 47 and valve 48 will not only supply $CO_2$, but water as well to the converter.

After preheating by heat exchanger 49, the feed to methanol converter 28 in line 50 enters the converter, is partially converted to methanol, as more fully described below by reference to FIG. 4, and leaves the converter 28 via line 51. Most of these gases are cooled in heat exchanger 49, while preferably a small stream of these converter offgases is directly utilized as a relatively hot stripping gas, by introduction into the bottom portion of the $CO_2$-stripping section 21 of the stripper-absorber 22 via line 52. Such direct use of converter offgases as stripping gas is highly advantageous as further explained below.

After cooling by heat exchanger 49, the converter offgases in line 53 are further cooled, and methanol (and relatively minor impurities such as water, dimethyl ether and ethanol) are condensed, in condenser-cooler 54, pass into separator 55 via line 43, and liquid from line 43 is separated from converter recycle gases in separator 55.

It is now seen that the present invention in contrast to conventional synthesis gas processes requires no large and expensive synthesis gas compressors. (The compressors required are mere blowers, to compensate for pressure drops in recycle flows). The reforming reaction, in spite of the adverse effect of pressure thereon, can be conducted in the same range of pressure as the conversion of synthesis gas, for example, to methanol. In part this is because of the autothermal nature of the reforming reaction, in which it is not necessary to transfer heat through temperature limited metal tubewalls from a combustion zone to an endothermic reforming zone. Other partially or wholly autothermal reforming processes are known but none has or even contemplates the high efficiencies of this present invention. Of course, as in all reforming reactions, these reactions cannot be carried fully to completion; i.e., some of the hydrocarbon to be reformed, mainly methane, remains. In the present invention at preferred conditions this unreformed methane in the relatively dry synthesis gas in line 40 is held below about 3 mol percent of the dry synthesis gas product of the reforming step, and preferably below about 2 mol percent. By virtue, however, of conversion reactions, such as methanol formation, in which liquid is formed and removed, and the gases recycled, this methane content—as well as that of any other inerts—"builds up", and if not removed will build up to deleteriously affect the conversion rate by drastically lowering the partial pressure of the reactants CO and $H_2$. These latter partial pressures are required to remain at substantial values because the reaction: $CO+2H_2=CH_3OH$ equilibrium varies in favor of methanol formation directly as the square of the hydrogen partial pressure and proportionate to carbon monoxide partial pressure, and the rates of conversion vary similarly. Thus, means for controlling inerts without excessive loss of yield is a most important part of the present invention.

Such inerts as argon, entering the system with the oxygen, and nitrogen which may enter both with the oxygen and in the natural gas, must, of course be removed by some means of purging from the methanol converter recycle gas to outside the system. Of course, on the other hand, in the case of ammonia production from hydrogen produced from the synthesis gas, by well-known steps, nitrogen is not an inert.

In the case of methanol synthesis from the synthesis gas, another complication is that it is generally found that, while a two to one ratio of $H_2$ to CO is required for methanol formation, a ratio of $H_2$ to CO which is quite appreciably greater is desired over the conversion catalyst. If the carbon monoxide concentration is too high relative to the hydrogen, it tends to inhibit the methanol formation rate, apparently by preferential adsorption of CO on the catalyst to the exclusion of sufficient hydrogen adsorption. At the same time, as previously mentioned, the present process produces a balance of hydrogen/carbon ratio just right for methanol production, i.e., essentially 2 to 1.

Accordingly, further objects of the invention are to simultaneously: purge inerts from the methanol conversion circuit in sufficient amount that their concentration over the catalyst is not excessive (i.e., methane, argon, nitrogen and $CO_2$ total content less than 20% as the gases leave the catalyst); purge an amount of combustible gases therefrom along with the inerts to outside the process which is no greater than the amount which can be usefully utilized in efficient means for generating the compressed oxygen supply (in conjunction with that steam which is available for power production from the process); permit a near stoichiometric production of hydrogen to carbon monoxide ratio; permit a greater than stoichiometric ratio over the methanol conversion catalyst; and yet, at the same time, not to lose excessive relative amounts of hydrogen by virtue of its higher than stoichiometric content in the converter circuit.

The simultaneous solution of these requirements, according to aspects of the present invention, is accomplished by several interacting means. First $CO_2$ in the synthesis gas is absorbed and recycled, as aforesaid. This keeps the $CO_2$ portion of the inerts low in the conversion circuit. It also causes the production of very little water in the methanol product, thereby lowering subsequent distillation requirements, reduces parasitic heat losses in subsequent uses of crude methanol in which it is vaporized, such as the MTG process previously mentioned, and significantly enhances the solvent power of the crude methanol used for absorption of various unwanted gaseous components.

Next, the methane—which is much more difficult to absorb from the synthesis gas in the manner of the $CO_2$ using crude methanol as the absorbent, since economically prohibitive amounts would be required—portion of the inerts is controlled by a combination of means. By utilizing the converter offgas in line 52 as stripping medium for recycle $CO_2$ stripping, the methane in this stream is returned to the reforming reactions in vessel 31 where it is usefully reformed. In the preferred embodiment this return is over about 50% of that entering the conversion circuit.

Then methane and other gases are absorbed in the product crude methanol which is separated from gas in the converter circuit in separator 55. In the preferred embodiment this absorption is augmented by the addition of recycle methanol to the converter offgases as they are being cooled and condensed in condenser-cooler 54. In FIG. 1 this is schematically shown as line 56. This procedure, over the extensive surface of condenser 54, essentially saturates the methanol with dissolved gases at relatively little additional capital or operating cost. Then the methanol from separator via line 57 is introduced to the bottom flash section 58 of stripper-absorber 22. In the preferred embodiment this flash section operates at a pressure just sufficiently high for the gaseous effluent from stripper-absorber 22 at line 59 to serve as fuel gas for a modern, relatively efficient gas turbine, i.e., about 17 ata. In flash section 58 a substantial portion of the dissolved gases nitrogen, argon, hydrogen, carbon monoxide and methane (but little $CO_2$ or heavier) flash out, and are ultimately utilized as fuel gas, as aforesaid. The total amount of combustible gases provided in this manner to fuel gas is controlled by the amount of recycle methanol added to this circuit at line 56. However, since a large fraction of these combustible gases is CO and $H_2$ desired for methanol conversion rather than fuel gas (i.e., processing "investment" has been performed on them) it may be desirable, depending primarily upon the nitrogen and argon contents of the conversion circuit gas, to flash less fuel gas at this point than is required for fuel. In these cases, it will be advantageous to supplement this flash gas directly by separate introduction of natural gas, as shown by line 60. This natural gas may be introduced either above the liquid in section 58, shown by line 61 and valve 62, or if argon and/or nitrogen contents are tending to build up too high values in the conversion circuit, to sparge natural gas into this liquid, schematically shown by line 63 and valve 64. Such a latter procedure will have the effect of lowering nitrogen and argon in the conversion circuit and raising methane—which however is partially removed by equilibration with the gas in cooler 54 and return to reforming vessel 31 (via line 52) and consumption therein.

This sparging operation will be most advantageous under conditions of relatively low operating pressure and relatively high argon/nitrogen inert levels.

Clearly, of course, these inerts removal means add operating flexibility to this process—particularly in the case of process upsets—which, because of its very high yield objective, is inherently a closely coupled process in several of its aspects. The advantageous reason for adding natural gas fuel through line 60 rather than directly to the gas turbine will be appparent below in reference to the operation of stripper-absorber 22.

It is now seen that the means employed to control inert levels in the converter circuit—by virtue of the lower solubility of hydrogen in methanol than other gases present—has the effect of conserving hydrogen in the system, thus allowing it to build up to a ratio to carbon monoxide which is greater than its ratio of production in the reforming vessel 31. Thus, in the preferred embodiment the ratio $H_2/CO$ in the reformed offgas in line 34 is about 1.95, while the ratio leaving the methanol converter in line 51 is about 2.68, and while, at the same time, the ratio in the fuel gas is substantially less than 2.

As shown in FIG. 1, it is preferred that the source of the methanol used to augment this flash-purge is methanol pumped back up to conversion pressure from flash section 58 via line 65 and pump 66. Only the amount of the net production of crude methanol enters the $CO_2$ absorption section 103 of separator-absorber vessel 41, via line 67. Other arrangements are possible, but this one tends to isolate the flash-purge methanol with its relatively high methane content from the methanol system used to absorb $CO_2$. In this way methane is little if any carried back into the synthesis make gas by equilibration with the $CO_2$-lean methanol entering vessel 41 via line 68. It is desired to reduce $H_2S$ and COS levels to the maximum extent possible with these streams; it is therefore preferred for line 67, rather than leading to admixing with the $CO_2$-lean methanol in line 68, to lead directly to the top of the absorption section, while the methanol in line 68 is introduced several stages in the absorption below that of line 67. In this way, $H_2S$ and COS are finally absorbed by essential S-free methanol, as produced in the methanol converter. Minimizing sulfur in the gases to the methanol converter (usually to well below 0.1 part per million) will, of course, lengthen catalyst life.

$CO_2$-rich methanol leaves vessel 41 via line 69 and at least a major portion is preheated by heat exchanger 70. It may be desired (not shown) to leave a relatively small portion cooler than the main portion and introduce it at a point higher in stripper-absorber 22 than the main stream, to act as a dephlegmator, thereby condensing methanol from the stripping gas in section 21. Such a procedure is well known.

In addition, it is preferred that the stripping gas from section 21 be scrubbed by process water condensate, such as that in line 38, in sponge section 71, in order to remove methanol from recycle gas in line 32, which is then circulated by blower 72. In order to minimize pumping and compression power requirements, it is preferred that $CO_2$-stripper 21 be operated in the same range of pressure as the methanol converter 28, as determined by the pressure drop in line 52. Alternatively blower 72 could be inserted in other locations, for example, in line 52, where the molar flow is less than in line 32, but the temperature is greater.

The stream in line 73 from the bottom of sponge section 71, comprising methanol and water, is flashed into the absorber section 74, along with scrubber bottoms in line 75. Flash gas therefrom, along with gases from riser 76, are scrubbed with process water condensate, such as that from line 38, to recover methanol therefrom and exit via line 59 as fuel gas. The bottoms from the absorber section 74 pass via line 77 and valve 78 to fractionator-stripper 20, where its methanol content is stripped out, as described below.

The $CO_2$-lean methanol from the bottom of $CO_2$-stripper section 21 passes via line 79 and pump 80 through heat exchanger 70 and water cooler 81. It is preferred that the net make of methanol remaining in this system be removed from the hot $CO_2$-lean methanol in line 79 through line 82 and valve 83, into methanol stripping section 84. This hot methanol (usually between about 320° F. and about 400° F.) contains relatively little dissolved gases, and is at such a high temperature that stripping of impurities such as dimethyl ether and lower boiling impurities therefrom is facilitated, using the gases from flash section 58. In this way, the second (low-boiling impurity) purification tower for methanol which is conventionally required will usually be rendered necessary, along with its energy requirements. Thus, the stripping here involved utilizes the "free" availability of the purge gas (which is essentially free of dimethyl ether and the like). And the heat content of the methanol heats said stripping gas, the resulting sensible heat of which is of course ultimately recovered in the combustion thereof, while the remaining heat content in the liquid methanol leaving stripping section 84 via line 85 and valve 86 is useful in its distillation in fractionator-stripper 20.

In the upper section of fractionator-stripper 20 methanol product is taken as overhead product via line 87, condenser 88, separator 89, pump 90, and line 91, while methanol reflux is returned to the tower via line 92. Dissolved gases, which are relatively very minor in amount, due to the aforesaid stripping operation on the methanol and the low solubility of these substances in the aqueous media in absorber section 74, the bottoms product of which enters fractionator-stripper 20 via line 77, exit from the system via line 93. These vent gases may be usefully utilized as fuel to a burner operating near atmospheric pressure which partially reheats combustion gases from the gas turbine (not shown) before said gases release sensible heat to a waste heat boiler (not shown), or they may be recompressed to gas turbine fuel gas pressure and introduced to this fuel gas system at an appropriate point.

In the lower, stripping section of fractionator-stripper 20, methanol is stripped primarily from water which has been used to scrub methanol from the various gaseous streams in the process. It is an important element of this invention to realize that this stripping is obtained at least to a substantial degree "free" in the sense that obtaining a given production of dry product methanol entails a certain boilup, and adding up to a certain substantial amount of the methanol partly as a relatively low concentration aqueous mixture requires no greater boilup; i.e., the stripping steam is already available. This is a further reason why: (1) the addition of the direct partial oxidation system—which recovers methanol by aqueous scrubbing—is so advantageous, and (2) the use of methanol as an absorbent—which is recovered in part by water scrubbing—is so advantageous.

Ethanol which may be produced as a minor impurity both in the partial oxidation (primarily from ethane) and in the catalytic conversion systems is preferably removed from the product methanol from the fractionator-stripper 20, as vapor side draw 95, at an intermediate point in the tower where the liquid phase is primarily aqueous and the methanol content is relatively low. It may be handled in the same way as vent gases from line 93, so that its heating value is recovered.

Formaldehyde and other impurities, which in aqueous (or methanolic) liquid phase are less volatile than methanol will tend to accumulate in the bottoms from fractionator-stripper 20, and part will be recycled to the partial oxidation scrubber section of vessel 10 via pump 96 and line 14. In the scrubber section of vessel 10, these impurities will equilibrate with the gas, and function as "recycle initiators" to the partial oxidation reaction, as previously explained. Excess scrubbing water in this system passes via line 97 through lines not shown, through preheater(s), symbolized by exchanger 35, and enters the waterside 98 of methanol converter 28 as shown, via line 99. This process water will be on somewhat the acid side due to the presence of some relatively slight amount of organic acids such as formic acid, and it is necessary that this circuit be of corrosion-resistant alloy. As detailed below, in reference to FIG. 4, this water and its volatile organic impurities will vaporize into the gases being saturated thereby, and the organic impurities therein will be destroyed at high temperature in reforming vessel 31, as aforesaid. Thus vessel 31 acts as a purifying means, and the water condensed from the offgases therefrom will contain none of these impurities. Excess water from the whole process may thus be taken therefrom as a relatively very pure water—except for dissolved gases such as $CO_2$, which may be removed in a deaerator (not shown).

REGENERATIVE HEAT EXCHANGER

Figure 2:
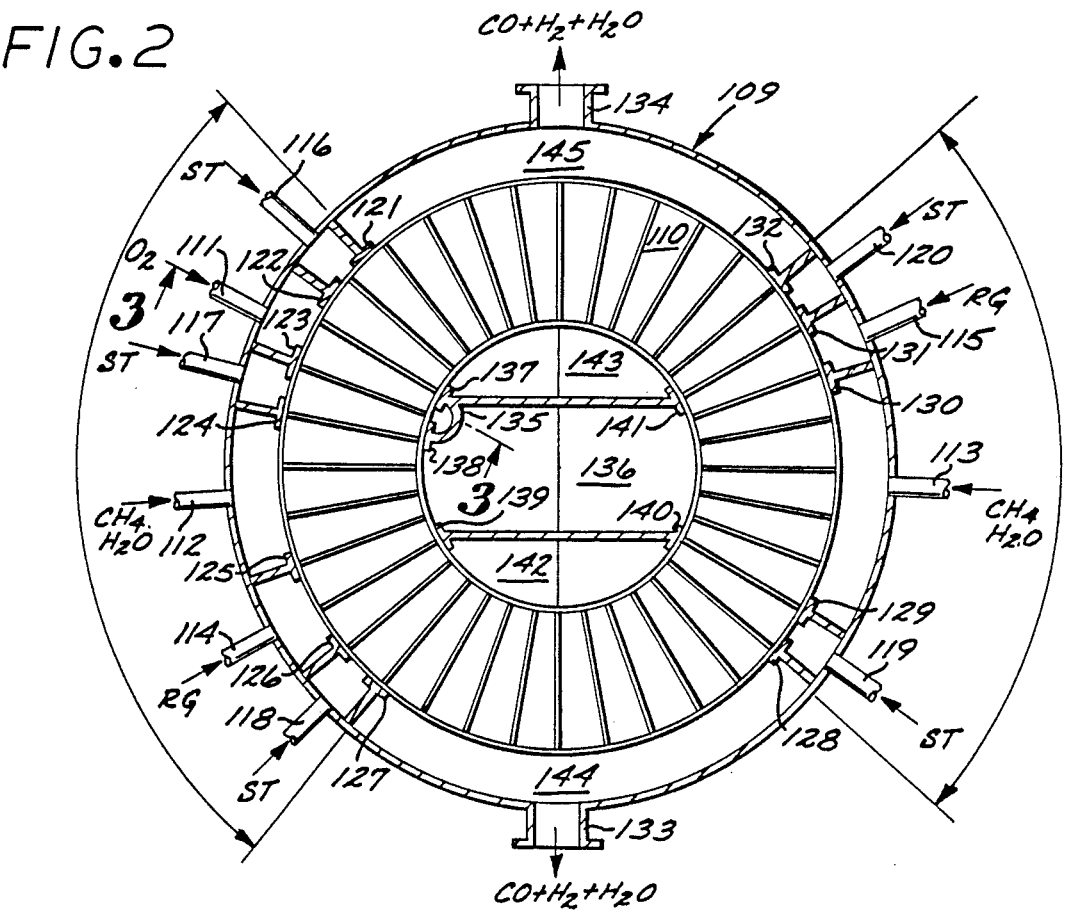
FIG. 2 is a schematic horizontal cross section taken on the line 2—2 in FIG. 1 showing the upper section of the preferred embodiment of the reforming vessel designated 31 in FIG. 1.

Referring to FIG. 2 showing a schematic cross section of the preferred rotary heat exchanger 109 of vessel 31, in which the feeds to vessel 31 comprising the hydrocarbon/steam mixture in line 30 of FIG. 1, recycle gas, and oxygen, are each preheated, while the vessel 31 product gas is cooled. This unit preferably comprises a rotating matrix 110 (preferably comprising heat-resistant ceramic fibers manufactured and compartmented in accordance with my said copending application appended hereto), oxygen inlet 111, mixture inlets 112 and 113, recycle gas inlets 114 and 115, and steam inlets 116, 117, 118, 119 and 120. Thus it is preferred that (except for the oxygen) the unit be approximately symmetrical about the centerline to the extent that the somewhat higher pressures of the inlet gases relative to the outlet gases be balanced on either side. Although separate sealing shoes 121 through 127 may be utilized, it is preferred to combine each pair of inlets together in a single unit, with passages and apertures therein for the various streams, and similarly with shoes 128 through 132.

Also shown are vessel 31 gas outlets 133 and 134, preheated oxygen collector gutter 135 and preheated hydrocarbonaceous collector plenum 136, along with seal shoes 137 through 141. Matrix 110 is divided into a suitable number of compartments to prevent cross-contamination of gases within the matrix. It is to be carefully noted that these compartments, as each rotates into position, must be essentially completely purged of combustible gases before introducing oxygen thereto and vice versa, utilizing steam streams as shown. It is also important that these steam streams be maintained at a higher pressure than the other streams so that leakage past the shoes is essentially only of steam rather than any other gases. At the inner shoes, this extra steam pressure communicated through the compartment from the outside may, with suitable width and positioning of the inner shoes 137 through 141, be relied upon to provide leakage of steam rather than other gases therefrom, or additional steam connections to these shoes and distributing grooves therein (not shown) may be employed.

Plenum 136 communicates by duct means to the inlet to reforming catalyst bed 100 shown in FIG. 1. The outlet from said bed communicates by duct means to plenums 142 and 143, and the reformed gas therein then passes out through matrix 110, is collected in plenums 144 and 145 and leaves the vessel through nozzle outlets 133 and 134.

Figure 3:
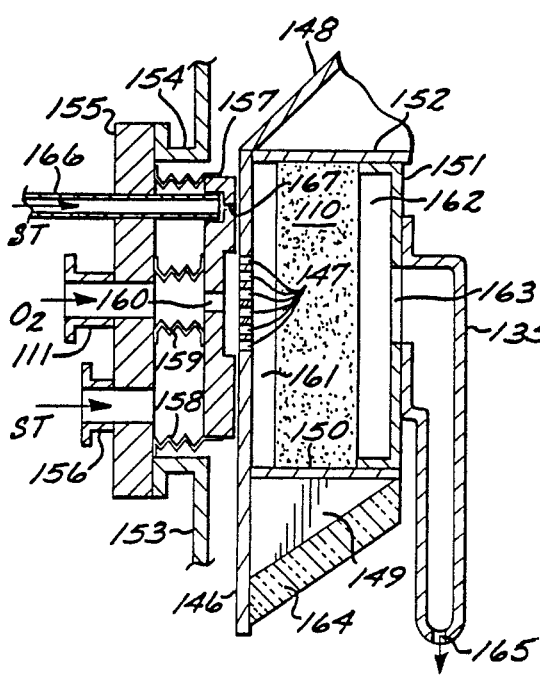
FIG. 3 is an enlarged, fragmentary vertical section taken on the line 3—3 of FIG. 2.

FIG. 3 illustrates a preferred variant of heat exchanger 109. The sectional view is taken along the line 3—3 through the plane of the oxygen inlet nozzle 111. It comprises rotating cylindrical shell 146 with holes 147, support cone 148 (attached to a driven shaft—not shown—at the centerline), gussets 149 supporting plate 150, matrix 110, ceramic core 151, plate 152, and insulation 164. The containing vessel 153 (which may be insulated internally and/or externally—not shown), has a large nozzle 154, to which is attached cover 155, carrying steam inlet nozzle 156 and oxygen nozzle 111 (as well as nozzles for the other inlet gases not seenin this view). The seal shoe 157 for all inlet gases (supported by means not shown) is made self-positioning by means of the gas contained in cylindrical bellows 158 and 159 exerting pressure upon shoe 157, which pressure is resisted by injecting a higher pressure, inert, stream, preferably steam, at a relatively small and fixed rate at several points between shoe 157 and rotating shell 146 (illustrated by the tube 166 and orifice 167), thereby maintaining a relatively fixed separation—of the order to thousandths of an inch—between them.

In operation according to the view seen in FIG. 3, oxygen passes in through nozzle 111, through the space surrounded by cylindrical bellows 159, hole 160 in shoe 157, and through holes 147; is distributed across the outer face of matrix 110 by plenum 161 and passes through matrix 110; is collected by plenum 162 and passes through hole 163 in core 151; and is collected by fixed oxygen gutter 135, which is terminated by a cylindrical section containing hole 165. Beyond this hole oxygen will meet a (combustible) mixture comprising a hydrocarbon gas and steam, and will therefore become an intense flame, which is directed into open space below it. In and after this flame, reforming of the hydrocarbonaceous gases will occur as described by reference to FIG. 1. Again it is emphasized that at all points of possible leakage along this oxygen path, means must be provided such that steam leaks into the path rather than oxygen or allowing other, combustible gases any opportunity to commingle with oxygen. It is also necessary that, in the event of failure for any reason of the oxygen flow, the oxygen path be completely swept out, in order that combustible gases do not back into this path. Such is readily accomplished by connecting a high pressure steam line to the oxygen line (through a selfactuating pressure reducing valve) immediately after a check valve at the outlet from the oxygen compressor. The pressure-reducing valve would be set to just back out at least the bulk of steam flow at the operating condition, i.e., preferably set at slightly less than operating oxygen pressure at the point of juncture. (Of course control interlocks for the process must be such that no operations can commence until steam is up to at least the pressure required at this point).

Controllable Temperature Catalytic Reactor

Figure 4:
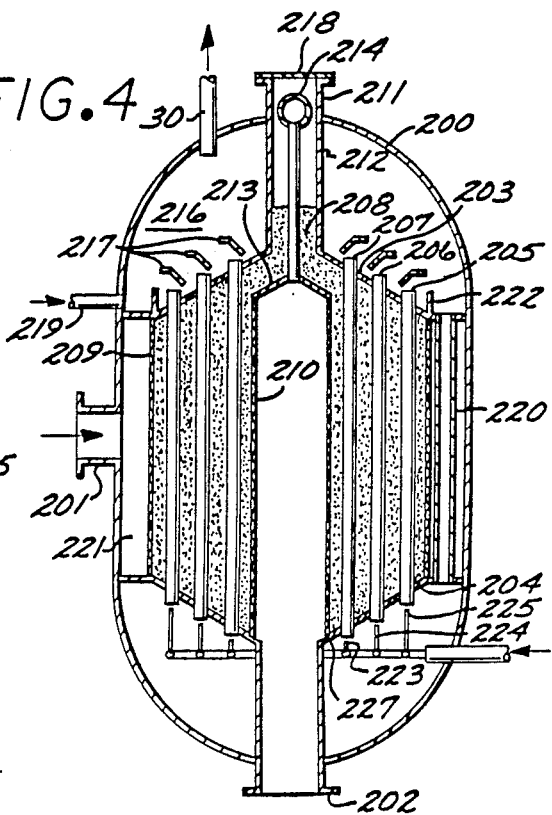
FIG. 4 is an enlarged vertical axial section of the preferred embodiment of the methanol converter designated 28 in FIG. 1.

In reference to FIG. 4, a side elevational cross section of the preferred embodiment of the controlled temperature catalytic reactor is shown. For the conversion of synthesis and other gases by catalytic means in which the reaction catalyzed is exothermic, this reactor has many advantages. First, it provides means on a large scale to hold exothermic catalytic reactions at essentially isothermal conditions. With such reactions such is important, since: (1) rates of these reactions increase substantially with increased temperature, but equilibrium towards desired products become less favorable with increased temperature; (2) with excessive temperature active catalysts tend to "sinter" and hence deactivate; and (3) recovered heat is more valuable the higher the temperature at which it is recovered (e.g., the higher the steam pressure and work available therefrom the higher the temperature).

Second, it readily provides advantageous means on a large scale to "program" and control an optimum temperature profile. Such is important since, in accordance with (1) above, when the reaction over the catalyst is far from equilibrium (i.e., near the gas feed entrance), the optimum temperature, in balancing rate with equilibrium considerations, is relatively high; while near the outlet, where product concentration is near a maximum, optimum temperature is relatively low.

Third, it provides means for stabilizing exothermic reactions. Such is important since: (1) if inlet temperatures are not high enough, or if inert levels are too high, the reaction will not "light off"; i.e., self-accelerate on the catalyst surface to the point at which it is self-sustaining in temperature; and (2) the valuable products are often an unstable intermediate in relation to possible exothermic reactions over a catalyst. For example, in the desired production of methanol, this product is intermediate in the sense both of the hydrogenation of carbon monoxide and of heat release to the production instead of methane, according to the reaction: $CO+2H_2=CH_4+H_2O+49$ Kcal. If the catalyst overheats and enters a dangerous region, the latter reaction self-accelerates, the temperature swiftly rises, and then not only is the catalyst ruined but in extreme cases the reactor itself may be irreparably damaged. Other examples of such possible adverse behavior include the oxidation of benzene or butane to desired maleic anhydride when the oxidation—and heat release—can tend to go much further; to undesired $CO_2$ and $H_2O$.

Fourth, it readily provides means for very large capacity catalytic converters. This is important since many of the industrially important reactions, including many reactions employing synthesis gas as an intermediate, such as the production of methanol and of ammonia, are conducted under relatively high pressure, it is economically and structurally important that all necessary features be enclosable in a vessel the diameter of which is small relative to its production capacity. Otherwise, production capacities become limited at a relatively low level by the thickness of structural walls becoming greater than can be fabricated by pressure vessel fabricating facilities. In the case of both methanol and ammonia production this has proved to be a problem limiting worldscale unit capacities, and costly and elaborate means have become necessary to circumvent this diameter size problem (e.g., the new, long, horizontal Pullman-Kellogg ammonia converter).

-Finally, it provides means for ease of, and quick, catalyst replacement. This is important because of limited catalyst life usually 2 to 5 years.

These and other objects are accomplished as described below. The reactor preferably comprises vessel 200; gas inlet/outlet nozzle 201 and 202; preferably conical tubesheets 203 and 204; tubes 205, 206 and 207; catalyst space 208 bounded radially by cylindrical catalyst screens 209 and 210; catalyst fill nozzle 211, nozzle cover 218, and standpipe 212; inner catalyst screen cover 213 and lift handle 214; liquid, preferably water, space 215 and liquid/gas disengaging space 216, preferably with baffles 217. In addition, the reactor comprises cooling liquid inlet 219, preferably distributing said liquid circumferentially by baffle 222, downcomers represented by 220, preferably located as indicated; i.e., communicating with the lower portion of space 216, and in circumferential plenum space 221, respectively. Downcomers 220 may also be placed radially inside screen 209.

Gas to be catalytically converted may pass along its path through the vessel in either direction, but it will usually be preferred for the gas to enter through nozzle 201, pass circumferentially around the reactor in plenum 221, enter screen 209, pass radially around the tubes and through the catalyst bed in space 208 and screen 210 and out through nozzle 202.

Used catalyst is conveniently emptied by simply removing an elbow (not shown) connected to and below nozzle 202, removing nozzle cover 218, hooking into lift handle 214, and lifting the inner screen 210. Catalyst will readily flow out, assisted by the slope of the preferably conical tubesheet 204 (and probably the use of a vibrator).

To refill, the screen 210 is dropped back and centered into place, preferably aided by circumferential notch 227, and the catalyst is poured in through nozzle 211. Relatively little breakup of catalyst during this fill operation will tend to occur, since first the free fall of the catalyst is arrested by screen cover 213, and second the tubes will tend to stabilize a very high angle of repose during the bulk of the catalyst filling operation, further reducing free fall distance. Catalyst fill above the screen 210 acts as a reservoir to replace gradual slump due to compaction, etc., thereby preventing any tendency for relatively untreated gases bypassing the catalyst.

Another important advantage of having conical tubesheets—aside from their much greater structural strength towards pressure differentials as compared to flat tubesheets—is that the radial gas flow is thereby kept at a more even velocity, the additional height towards the centerline tending to compensate for reduced circumferential flow cross section. This feature together with the fact that the flow path is relatively short, causes pressure drop through the bed to be minimal.

A very important aspect of the invention is that the heat release occurring within the catalyst is transferred to and is absorbed by liquid which is held to a near uniform temperature, preferably by its vaporization. Furthermore, in the case of methanol production, using modern active so-called "low temperature" catalysts, steam which is thereby produced can be utilized directly in the reforming to form the synthesis gas without the necessity of thereafter having to compress the synthesis gas to subsequent converter reactor pressure. Heretofore such that has not been practical. It is achieved in the methanol conversion reactor of the present invention by injecting the gas to be reformed into water space 215 through nozzles 223, 224 and 225. Water vapor is thereby vaporized directly into the gas during its passage up through the heated tubes. Thus it is practical to operate the catalyst towards the gas outlet therefrom at the equilibrium-favorable temperature as low as, for example, 500° F., while water is being vaporized at about 470° F., at a total pressure of over 60 ata, whereas the vapor pressure of water at 470° F. is only about 35 ata. By contrast, if pure steam were generated in this converter and admixed with gas to be reformed, the relatively large-volume product synthesis gas would have to be compressed from below 35 ata to the conversion pressure of 60 ata, requiring large and expensive compressors as well as power.

Furthermore, even though total pressure is constant throughout the waterside of the reactor, the temperature within the catalyst bed may be controlled and varied to obtain a desired temperature profile within the catalyst bed along its flow path. Such a desirable profile in an exothermic catalytic reaction limited by reaction rate near the inlet zone and equilibrium near the outlet zone is for the temperature to be relatively high in the inlet zone and relatively low in the outlet zone, with intermediate temperatures in between. With the reactor of the present invention, such is readily obtained by varying the relative gas flow to the tubes. Thus the desirable temperature profile is obtained by varying the size of the gas nozzles in a radial direction, nozzles 225 feeding tubes near the inlet zone of the converter gas being the smallest in gas flow aperture, nozzles 224 larger, and nozzles 223 largest. Of course nozzle sizes appropriate will also be determined by the heat release rate of the catalyst locally surrounding the tubes. Thus as the reaction proceeds along the radial converter gas flow path, and particularly in the case of the desired temperature profile, the reaction rate diminishes, and the heat release rate proportionately. Preferably this occurrence will be at least partially compensated for by varying the tube spacing. Thus the tubes will be relatively closer together in the inlet zone. And it may be desirable to provide external fins on at least some of the tubes. (It is to be noted that the direction of converter gas flow preferred, i.e., radially inward, is also advantageous in that relatively fewer tubes towards the centerline also provides a relatively larger cross section for flow, and thus also helps to even out converter gas velocities).

Also, simply by erecting cylindrical partition means (not shown), in the waterside of the reactor, it is clear that steam unmixed with gas may be generated to the extent that heat beyond that required for saturating the gas is available, and that the pressure of such steam (and consequently the temperature within the portion of the catalyst bed cooled thereby), may be independently varied.

It is now also seen that this reactor solves any "light-off" problems, particularly since the gas flow in the tubes will induce relatively very rapid circulation of the water through downcomers 220 and up through the sparged tubes. This circulation will cause the tubes, the catalyst and the converter gas to be brought up to at least near the water temperature, thereby providing quick startup and stability to the reactor.

Finally, it is now seen that the reactor of the present invention does not suffer from the capacity limitations of other commonly used reactors. Thus, the capacity of the multiple-stacked beds of the Imperial Chemical Industries cylindrical reactor can only be enlarged—at a given diameter—by increasing bed depths and utilizing higher gas velocities, both of which tend to increase pressure drops excessively. And the Lurgi reactor, in which converter gases flow inside catalyst-filled tubes which are cooled by boiling water, also can be increased in capacity at a given diameter only by lengthening the tubes and increasing gas velocities, again leading to excessive pressure drops. In contrast, in the case of the subject reactor, increased capacities are achieved merely by increasing the height of the reactor and thereby the cross section for flow, without increasing the pressure drop of the converter gas. (At the same time, at some relatively very large capacity, undoubtedly several times that of existing reactors, the increasing temperature difference from bottom to top of the cooling liquid/gas mixture flowing upward may become undesirable, and tend to limit further increase in size and capacity).

EXAMPLE

A plant for the production of methanol from methane according to the preferred embodiment of the invention operating at about 60 ata pressure and at a production rate of 1000 metric tons per day uses about 506 metric tons per day of oxygen, which is obtained by cryogenic separation of air compressed by a gas turbine and compressed by centrifugal compressors driven by a steam turbine supplied by steam from the generation of steam within the process and by economically utilizing sensible heat contained in the exhaust gases from the gas turbine. The gas turbine fuel is supplied from fuel gas at about 17 ata, mainly obtained from the required purge of inerts from the catalytic converter offgas.

By direct partial oxidation, substantial heat for the process is provided, along with over about 110 metric tons per day of methanol. Autothermal synthesis gas formation over secondary reforming catalyst 100 takes place at about 60 ata and down to about 2000° F.; it is then cooled by the rotary regenerator 109 to about 600° F. In this still-wet, reformed offgas the residual methane content is about 0.75 mol percent, requiring a mols steam/atom of total carbon ratio in the total feed to the reformer vessel 31 of only about 0.99, yet the reformer gas composition is well away from any tendency to deposit carbon on the reforming catalyst 100, in part because about 24.5% of the carbon atoms fed to the reformer vessel 31 is recycled carbon dioxide.

Total yield of methanol from this process is over about 93.2% of the total-and-fuel methane, including the provision of all required fuel to the gas turbine. This yield corresponds to less than about 23.2 million BTU of lower heating value of feed and fuel per short ton of product methanol.

Although in this specification the more preferred means of accomplishing the objects of the invention are described in detail, it will be clear to those skilled in the arts involved that various substitute means may also be employed within the scope of the invention. For example, in respect to the process aspect of the invention, it is clear that, although a rotating regenerator is to be preferred by virtue of the advantages cited, other means of preheating, reacting and quenching, such as fixed bed, switching regenerators, or recuperators may be employed, albeit less advantageously. Thus, the invention is not limited except as hereinafter stated in the claims.

I claim:

1. A method for the production of a synthesis gas comprising carbon monoxide and hydrogen from a hydrocarbonaceous gas, which comprises:

preheating said hydrocarbonaceous gas by heat exchange with said synthesis gas to a temperature in excess of approximately 1500° F., reacting said hydrocarbonaceous gas with oxygen in the presence of steam, thereby further heating said hydrocarbonaceous gas; and reforming said hydrocarbonaceous gas, thereby producing said synthesis gas.

2. The method of claim 1, wherein water vapor is added to the hydrocarbonaceous gas by passing said hydrocarbonaceous gas along with liquid water in heat exchange relationship to a heat-producing catalytic reaction of gases derived from said synthesis gas.

3. The method of claim 2, wherein said heat-producing catalytic reaction is the conversion of synthesis gas to methanol.

* * * * *